US010556051B2

(12) United States Patent
Appel et al.

(10) Patent No.: US 10,556,051 B2
(45) Date of Patent: Feb. 11, 2020

(54) MEDICAL DEVICE WITH OPERATOR SUPPORT

(71) Applicant: Fresenius Medical Care Deutschland GmbH, Bad Homburg (DE)

(72) Inventors: Jan-Willem Appel, Veitshöchheim (DE); Jürgen Klewinghaus, Oberursel (DE); Stefan Rudolph, Werningshausen (DE); Alexander Schrörs, Frankfurt (DE); Georg Verch, Wiesbaden (DE); Stefan Wittzack, Frankfurt (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 241 days.

(21) Appl. No.: 15/295,466

(22) Filed: Oct. 17, 2016

(65) Prior Publication Data
US 2017/0128648 A1　May 11, 2017

(30) Foreign Application Priority Data
Nov. 11, 2015　(DE) .................. 10 2015 014 527

(51) Int. Cl.
*A61M 1/16* (2006.01)
*A61M 1/14* (2006.01)
(Continued)

(52) U.S. Cl.
CPC ............ *A61M 1/1601* (2014.02); *A61M 1/14* (2013.01); *G05B 15/02* (2013.01); *G16H 40/63* (2018.01); *A61M 2205/505* (2013.01)

(58) Field of Classification Search
CPC .......... G16H 40/63; A61M 1/14; A61M 1/16; A61M 1/1601; G05B 15/02
See application file for complete search history.

(56) References Cited

U.S. PATENT DOCUMENTS

| 5,970,457 A | 10/1999 | Brant et al. |
| 6,676,621 B1 | 1/2004 | Menninger |
| (Continued) | | |

FOREIGN PATENT DOCUMENTS

| DE | 19624988 A1 | 1/1998 |
| DE | 10 2011 121668 A1 | 6/2013 |
| (Continued) | | |

OTHER PUBLICATIONS

International Patent Application No. PCT/EP2016/077151, International Search Report (dated Feb. 7, 2017).

*Primary Examiner* — Tuan C Dao
(74) *Attorney, Agent, or Firm* — Leydig, Voit & Mayer, Ltd.

(57) ABSTRACT

A medical device includes: at least one input device; at least one output device; at least one operating component; and a control unit. The control unit has data access to at least one file pertaining to the medical device, wherein text passages or graphics of the at least one file pertaining to an operating component are selectable. The control unit is configured to, after selection of a text passage or a graphic, cause at least one operating parameter of the operating component and/or at least one output variable that is created by the operating component to be read out as output, and/or facilitate input of an adjustable operating parameter for the operating component.

21 Claims, 5 Drawing Sheets

(51) Int. Cl.
*G16H 40/63* (2018.01)
*G05B 15/02* (2006.01)

(56) References Cited

U.S. PATENT DOCUMENTS

| | | | |
|---|---|---|---|
| 6,738,052 B1 | 5/2004 | Manke et al. | |
| 7,286,992 B2 | 10/2007 | Sander et al. | |
| 10,154,097 B2 | 12/2018 | Wang et al. | |
| 2001/0032100 A1* | 10/2001 | Mahmud | G06F 19/3418 705/2 |
| 2003/0233348 A1* | 12/2003 | Franklin | G06F 16/93 |
| 2004/0254928 A1* | 12/2004 | Vronay | G06F 16/243 |
| 2007/0260213 A1* | 11/2007 | Williams | A61M 5/172 604/500 |
| 2008/0238666 A1* | 10/2008 | Loncar | G06F 19/3456 340/540 |
| 2009/0113335 A1 | 4/2009 | Sandoe et al. | |
| 2009/0228825 A1* | 9/2009 | Van Os | G06F 3/0488 715/780 |
| 2011/0173028 A1* | 7/2011 | Bond | G06Q 10/08 705/3 |
| 2011/0178820 A1* | 7/2011 | Soni | A61B 5/0002 705/3 |
| 2012/0022354 A1* | 1/2012 | Beyer | A61B 5/02035 600/365 |
| 2012/0209624 A1* | 8/2012 | Maitland | G06Q 50/24 705/3 |
| 2014/0114649 A1* | 4/2014 | Zuev | G06F 17/289 704/9 |
| 2014/0230071 A1 | 8/2014 | Adam et al. | |
| 2015/0111190 A1* | 4/2015 | Vittorio | G06F 16/9535 434/319 |

FOREIGN PATENT DOCUMENTS

| | | |
|---|---|---|
| DE | 10 2012 020945 A1 | 4/2014 |
| EP | 0 904 788 A1 | 3/1999 |

* cited by examiner

MEDICAL DEVICE WITH OPERATOR SUPPORT

CROSS-REFERENCE TO RELATED APPLICATIONS

Priority is claimed to German Patent Application No. DE 102015014527.4, filed on Nov. 11, 2015, the entire disclosure of which is hereby incorporated by reference herein.

FIELD

The invention relates to the field of medical devices, in particular dialysis machines, with a user interface.

BACKGROUND

Medical devices are often equipped with a user interface for input and output of information. The usual user interfaces are display screens such as liquid crystal (LC) screens, thin-film transistor (TFT) screens or organic light-emitting diode (OLED) screens, which may be implemented with or without touchscreen functionality. In addition to display of information, touchscreen displays also offer a convenient and variable input option for information when the user touches the touchscreen surface with a finger, and due to the flat design, they also offer a surface that is easy to clean and is therefore hygienic.

Medical devices are frequently also equipped with a variety of other devices for information output and for information input. Therefore, acoustic signals can be output via a loudspeaker. Acoustic input may be carried out via microphones. Optical sensors such as fingerprint scanners or cameras for detecting optical features may also be part of medical devices.

For operation of medical devices, special graphical user guides are often utilized, preferably embodied as graphical user interfaces (GUIs), Such screen-based user guides usually have a predetermined structure with menu views, among which certain functions are combined, for example, the display of measured values or input options for parameters to he set, such as pump rates or the like.

A menu view is defined here as the display of certain information at a given point in time. The information displayed here also includes menu points for adjustment of parameters. For example, a menu may include the display of a pump rate of a certain pump of the medical device, and also the display of a menu point that can be activated by the operator, after which the operator can then enter and/or adjust the pump rate. In the case of graphical user interfaces on devices having a touchscreen display, menu points are usually selected by touching the activation surfaces (so-called touch keys) that are kept for these menu points.

Medical devices may also provide a symbolic representation of the respective device parts to be adjusted, such as pumps, on a touchscreen display, where the input of a parameter for this part of the device is made possible through direct contact with the symbol—for example, as described in U.S. Pat. No. 6,738,052, the entire disclosure of which is hereby incorporated by reference herein.

As a rule, the graphical user interface will show a plurality of menu views in order to be able to represent a plurality of information items pertaining to the medical device and input options in a comprehensive and thematically organized manner. To retrieve certain menu views, so-called jump labels can be provided; these can be activated by the user and refer to individual submenu views from a main menu, for example. There are also known jump labels that refer between individual submenu views.

The graphical user interface of the medical device may be designed with different degrees of complexity for different operating modes of the device. For example, in a so-called service mode, the graphical user guide may have a particularly great complexity, because in this mode, access to a particularly varied range of input options and information pertaining to the medical device should be enabled for the operator, for example, a service technician.

Other operating modes that may involve adapted graphical user guides, for example, pertain to the operation by application consultants, trainers or developers of the medical device. The respective graphical user interfaces are adapted to the needs of the respective user and may each have a different degree of complexity.

In such operating modes, numerous special functions can be made available for operation, adjustment maintenance and diagnosis of the device in the respective graphical user interface, and these special functions are not made available to a patient during normal operation of the medical device in treatment of a patient. Discovering certain information or an input option in the graphical user interface has in most cases become increasingly difficult with the increasing the complexity of the graphical user interface.

Thus, certain information or input options, depending on which menu view is currently being displayed, cannot be selected directly by user input. In such cases the specific information or input option is not part of the current menu or submenu view. The user may optionally have to go through multiple user inputs to a menu view and/or a submenu view, which includes certain information or input options. The number of user inputs necessary for this increases potentially with the complexity of the graphical user interface.

The user searching for specific information or wanting to operate a specific input on the medical device must accordingly know in which menu view this information is displayed and/or in which menu view the input option is located for the input being sought by the user.

This requires extensive training and/or experience in handling the medical device.

SUMMARY

In an exemplary embodiment, the invention provides a medical device, comprising: at least one input device, configured for input of information pertaining to the medical device; at least one output device, configured for output of information pertaining to the medical device; at least one operating component, wherein the at least one operating component has at least one operating parameter that can be adjusted and/or read out, and/or has at least one output variable that is created by the operating component and can be read out; and a control unit, connected to the at least one operating component and the at least one input device and the at least one output device, wherein the control unit is configured to output information pertaining to the medical device via the at least one output device and to provide input options for adjustable operating parameters. The control unit has data access to at least one file pertaining to the medical device, wherein text passages or graphics of the at least one file pertaining to an operating component are selectable. The control unit is configured to, after selection of a text passage or a graphic, cause at least one operating parameter of the operating component and/or at least one output variable that is created by the operating component to be read out as output, and/or facilitate input of an adjustable operating parameter for the operating component.

In another exemplary embodiment, the invention provides a method for input and output of information pertaining to a medical device, the method comprising: outputting, by the medical device, information pertaining to the medical device; providing, by the medical device, input options for adjustable operating parameters of operating components of the medical device; receiving, by the medical device, a selection of a text passage or graphic of at least one file pertaining to an operating component of the medical device; and outputting, by the medical device, at least one operating parameter of the operating component and/or at least one output variable that is created by the operating component, and/or facilitating, by the medical device, input of an adjustable operating parameter for the operating component.

BRIEF DESCRIPTION OF THE DRAWINGS

The present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following.

DETAILED DESCRIPTION OF THE FIGURES

Embodiments of the present invention simplify the operation of medical devices and make them more reliable.

Exemplary embodiments include a medical device and a method for a medical device. In an exemplary embodiment, the medical device comprises at least one input device, which is equipped for input of information pertaining to the medical device, and wherein the medical device comprises at least one output device, which is equipped for output of information pertaining to the medical device. The medical device comprises at least one operating component, which may be embodied as an actuator or a sensor, for example. Such an operating component will have an operating parameter that can be adjusted and/or read out, such as, for example, a delivery rate of a pump and/or an output variable that is created by the operating component and can be read out, such as a sensor value of a pressure sensor, for example.

In addition, the medical device includes a control unit, which is connected at least indirectly to the at least one operating component and the at least one input device and the at least one output device by data technology, wherein the control unit is configured to output information pertaining to the medical device and to keep input options available for the adjustable operating parameters.

The control unit has technical data access to at least one data file pertaining to the medical device. Technical data access can be implemented via a network connection. According to another embodiment the data file is to be stored in a data memory of the medical device, to which the control unit has data access. According to another embodiment, the at least one file is stored in the data memory of the medical device via a network connection. The at least one file pertaining to the medical device is a saved document, for example, operating instructions, with text and graphic components in one embodiment.

The control unit is configured so that text passages or graphics pertaining to an operating component, of the at least one file pertaining to the medical device can be selected.

Such a text passage pertaining to the operating component may be, for example, a single term, which designates an operating component, for example, a "blood pump." However, several words that belong together, such as a sentence relating to an operating component, can be selected, for example, "adjustment of the blood pump rate." A graphical insert pertaining to an operating component may be, for example, an illustration of the corresponding operating component or a symbolic representation, for example, a symbol in a hydraulic diagram.

After selecting such a text passage or such a graphical insert, at least one operating parameter of the operating component and/or at least one output variable that is created and can be read out by the respective operating component can be output. This may be, for example, a sensor value, for example, a blood pressure sensor.

After selecting such a text passage or such a graphic, the input of an operating parameter that can be set for the respective operating component can be enabled, such as, for example, for the delivery rate of a blood pump to be adjusted.

In one embodiment, the at least one file pertaining to the medical device includes exclusively text-based and/or graphic-based information, such as, for example, operating instructions or a technical handbook stored digitally in the file. The file in this case does not include any executable program code that could be used to control the medical device.

The present invention is explained below on the example of a dialysis machine as an example of an embodiment of a medical device.

Dialysis machines are blood treatment machines, in which a fluid from a patient is supplied through a fluid line to a fluid treatment component, by means of which the fluid treatment component is treated and returned back to the patient over the fluid line, which can be divided into an arterial branch and a venous branch. Examples of such blood treatment machines include hemodialysis machines in particular. Such a blood treatment machine is described, for example, in U.S. Pat. No. 6,676,621, the entire disclosure of which is hereby incorporated by reference herein.

Dialysis is a method for purifying the blood of patients with acute or chronic renal failure. A fundamental distinction is made here between a method having an extracorporeal blood circulation, such as hemodialysis, hemofiltration or hemodiafiltration, and peritoneal dialysis, which does not have an extracorporeal blood circulation.

In hemodialysis, blood is carried in an extracorporeal circulation through the blood chamber of a dialyzer, which is separated by a semipermeable membrane from a dialysis liquid chamber. Dialysis liquid containing the blood electrolytes in a certain concentration flows through the dialysis liquid chamber. The substance concentration of the blood electrolytes in the dialysis liquid corresponds to the concentration in the blood of a healthy subject. During the treatment, the patient's blood and the dialysis liquid are generally passed by both sides of the semipermeable membrane in countercurrent at a predetermined flow rate. The substances that must be eliminated in urine diffuse though the membrane from the blood chamber into the chamber for dialysis fluid, while at the same time electrolytes present in the blood and in the dialysis fluid diffuse from the chamber of the higher concentration to the chamber of the lower concentration. If a pressure gradient is built up on the dialysis membrane from the blood side to the dialysate side, for example, by means of a pump, which draws dialysate from the dialysate circulation on the dialysate side downstream from the dialysis filter, then water goes from the patient's blood through the dialysis membrane and into the dialysate circulation. This ultrafiltration process leads to the desired removal of water from the patient's blood.

In hemofiltration, ultrafiltrate is withdrawn from the patient's blood by applying a transmembrane pressure in the dialyzer, without passing the dialysis liquid by on the side of the membrane of the dialyzer opposite the patient's blood. In addition, a sterile and pyrogen-free substituate solution is added to the patient's blood. We speak of predilution or post-dilution, depending on whether this substituate solution is added upstream or downstream from the dialyzer. In hemofiltration, the mass exchange takes place by convection.

Hemodiafiltration combines the methods of hemodialysis and hemofiltration. This involves both diffusive mass exchange between the patient's blood and the dialysis liquid via the semipermeable membrane of a dialyzer as well as filtering the plasma water through a pressure gradient applied to the membrane of the dialyzer.

The methods of hemodialysis, hemofiltration and hemodfiltration are usually carried out with automatic hemodialysis machines, such as those distributed by the present patent applicant under the designation 5008, for example.

Plasmapheresis is a blood treatment method in which the patient's blood is separated into blood plasma and its corpuscular constituents (cells). The separated blood plasma is purified or replaced by a substitution solution, and the purified blood plasma or the substitution solution is sent back to the patient.

In peritoneal dialysis, a patient's abdominal cavity is filled with dialysis liquid having a concentration gradient with respect to the endogenous liquids, this filling taking place via a catheter passing through the peritoneum. Toxic substances present in the patient's body enter the abdominal cavity via the peritoneum, which acts as a membrane. After a few hours, the dialysis fluid in the patient's abdominal cavity, which is now spent fluid, is replaced. Water can go from the patient through the peritoneum into the dialysis liquid through osmotic processes and can thus withdraw water from the patient.

The method of peritoneal dialysis is usually carried out with the help of automatic peritoneal dialysis machines such as those distributed by the present applicant, for example, under the brand name sleep•safe.

Dialysis machines, as one example of complex medical machines, have numerous functions. To control these functions, medical devices such as dialysis machines are equipped with at least one control unit. These may be embodied is a CPU (central processing unit) or a microcontroller, programmed with software programs. In light of the disclosure of the present invention, it is not important whether the methods described are carried out by one or more control units. Accordingly, several control units are also considered to be one control unit as long as they are interconnected with regard to data technology. The software programs are usually kept in an internal memory device. Additional memory devices may be kept for storing other information, such as treatment data.

Medical equipment such as dialysis machines may have network interfaces for data connection to external devices.

Dialysis machines are frequently operated using graphical user guides, which may be embodied as a touchscreen display. These use graphical user guides, which may be embodied as a graphical user interface (GUI). Such screen-based user guides usually have a predetermined structure with menu views, which combine certain functions, for example, the display of measured values or input options for parameters to be set such as pump rates or the like, for example.

A graphical user interface, embodied as a touchscreen display, is an input and output device in the sense of the present invention. An alternative embodiment provides for the graphical user interface to be embodied on separate input and output devices, for example, by means of a display and a touchpad separate from the display.

Another possibility for operation of the medical device comprises acoustic voice input and/or output. Those skilled in the art make use here of the known methods of technical voice creation in voice output by the medical device and voice recognition in input of voice by the user. An input device in the sense of the present invention may thus be a device for input of acoustic information and may be embodied for example, as a microphone. An output device in the sense of the present invention may thus be a device for output of acoustic information and may be embodied as a loudspeaker, for example.

The medical device comprises at least one input device, which is equipped for input of information pertaining to the medical device and at least one output device, which is equipped for output of information pertaining to the medical device.

It is possible to provide for the input and/or output of information pertaining to the medical device to take place by means of a single input device and/or by means of a single output device. In an alternative embodiment, the input and/or output of information pertaining to the medical device take(s) place by means of multiple input devices and/or by means of multiple output devices.

To make the operation of the dialysis machine simpler and more reliable, the present invention provides that information pertaining to the medical device, namely the dialysis machine here, be kept in digital form as at least one file, to which the dialysis machine has data access, wherein text passages or graphics pertaining to the operating component of the file can be selected.

In the sense of the present invention, the at least one file is also understood to he a databank structure, in which information pertaining to the medical device is stored.

The selectability of such a text passage of the at least one file pertaining to the medical device may take place through a table of contents of words pertaining to the operating component, for example, wherein the selection is made, for example, by user input by touching a word from the index on a touchscreen display (finger touch).

In an alternative embodiment, selectable text passages of the at least one file pertaining to the medical device can be displayed in a thematic organization, for example, headings of selectable text passages pertaining to the equipment of the dialysis machine can be displayed together, Such an organized display of headings of selectable text passages can take place for example, through selection of the corresponding generic term (here, for example, "equipment" or "equipment of the dialysis machine") in an index of words as described above.

Another embodiment provides for text passages or graphics pertaining to operating component to be part of a detail of the at least one file pertaining to the medical device displayed on the graphical user interface, which can in turn be selected. Such excerpts of the at least one file pertaining to the medical device may include, for example, single pages or entire chapters of operating instructions stored digitally or a technical handbook.

In addition, a search function that can be retrieved via the user interface can also be implemented, wherein the at least one file can be searched for text strings by using this search function. A text string may be a single word or part of a word or several words together. Text strings found by the search function may be selectable in particular when the text string pertains to an operating component.

In light of the disclosure of the present invention, the input and/or output of information, for example, the input of a text string, may also take place at least partially through acoustic, signals in the form of speech. For example, the user can also speak a selected text string and thus perform a voice input. The medical device in this case is equipped with a microphone and is configured, so that the voice input is digitized by using voice recognition methods with which those skilled in the art are familiar and is sent in this way to the control unit as an input text string. Information output may take place in the same way through the medical device and also at least partially via voice output.

Medical devices with voice output and voice control of at least individual functions of the medical device are familiar to those skilled in the art, for example, as described in German Patent No. DE 196 24 988 A1, U.S. Pat. Nos. 5,970,457 and 7,286,992, the entire disclosures of which are hereby incorporated by reference herein. The embodiments of the present invention described below can at least partially access spoken language for the input and output of information.

An operating component in the sense of the present invention is a part of the medical device, which is connected by signal technology at least indirectly to a control unit of the medical device. Such operating component may include, for example, actuators such as motors, pumps and valves as well as sensors, such as temperature sensors or blood pressure sensors. An operating component may also include accessory parts or add-on parts of the medical device, which are connected by signal technology at least indirectly to a control unit of the medical device.

In one embodiment, the operating component can be adjustable with regard to an operating parameter. For example, a valve can be controlled to open or to close or a pump can be controlled, so that a certain pump rate is established.

In another embodiment, an operating component may also generate output variables. This is the case with sensors in particular. The output variable of a blood pressure sensor, which is mounted on the extracorporeal blood circulation of a dialysis machine, is, for example, the liquid pressure, which is prevailing precisely at this location in the extracorporeal blood circulation, measured in the blood, and/or an output variable that is characteristic thereof, for example, a characteristic electric voltage or a characteristic electric resistance.

One example of an operating component that can be adjusted as well as generating output variables itself is a peristaltic pump having a sensor for detecting the rotational rate of the rotor arm. The motor of the peristaltic pump can be controlled by the control unit to set a certain rotational rate of the rotor arm to thus generate a certain pump rate as a function of the tube inserted.

The sensor for detecting the rotational rate of the rotor arm detects the actual rotational rate of the rotor arm. This information can be used for example, to retain, even under a heavy load, a rotational rate that has been set, and to do so by feedback of the actual variable to the control unit, which then adjusts the control of the pump motor subsequently.

The operating component in the sense of the invention can also be characterized by operating parameters, which are adjustable and/or can be read out, such as, for example, the rotational rate of the rotor arm of a peristaltic pump and/or output variables that can be read out, such as the blood pressure measured by a blood pressure sensor.

In the simplest case, a text passage of the file relating to the operating component can be a designation of the operating component, for example, "blood pump." In addition, several words that belong together, for example, "adjusting the blood pump," may be a text passage of the part of the file displayed, pertaining to the operating component.

A graphic within the file pertaining to one operating component may be, for example, an illustration of the corresponding operating component or a symbolic representation, for example, a symbol in a hydraulic diagram. To facilitate the discovery of the respective operating component by the user in such a hydraulic diagram or in technical diagrams in general, it can be displayed with graphical emphasis, for example, by a frame, a certain color, a flashing diagram or by arrows pointing to the component.

The user of a medical device is interested in learning or adjusting the operating parameters of the medical device in a simple and rapid manner. Simple and rapid and therefore also reliable operability on the medical device is ensured by the selectability of text passages or graphics, as proposed in accordance with the present teaching, pertaining to an operating component, according to which the selected operating component can be adjusted or an output variable generated by the selected operating component can be displayed.

The user of the medical device can therefore search for the text string "blood pump," for example, by using the search function within the at least one accessible file when the user would like to check and/or adjust the blood pump rate. In one embodiment, the search function thus offers corresponding excerpts of the file, which include this text string. Within such an excerpt of the file, the text string "blood pump" as a text passage pertaining to one operating component of a displayed excerpt of the file itself can in turn be selected. An excerpt of the file that is displayed may be, for example, a page or a chapter of operating instructions or of a technical handbook.

If the user selects such a text passage that pertains to an operating component within the selected excerpt of the file, then the present teaching proposes that the graphical user interface can display the operating parameters of the respective operating component, i.e., for example, the set rotational rate of the blood pump, which is embodied as a peristaltic pump, and/or at least one output variable that is created and can be read out by the respective operating component, for example, the actual rotational rate, which has been detected by the sensor for detection of the rotational rate of the rotor arm of the blood pump.

Furthermore, as an alternative or in addition to the display of the operating parameter described here, an input option for the adjustable operating parameters of the respective operating component, i.e., for example, a window that permits input of a rotational rate for the blood pump, can also be displayed on the graphical user interface after selection of a text passage or a graphic within the displayed portion of the file pertaining to an operating component.

In an alternative embodiment, the search function may also offer text passages pertaining to an operating component and designated by the text string entered (for example, "blood pump") for selection directly. Therefore, it is not absolutely necessary to display a page or a chapter of operating instructions or a technical handbook containing a text string pertaining to the corresponding operating component as an excerpt of the data file. The operating component can be selected directly accordingly.

It is provided that the search function can be retrieved as directly as possible within the structured user guide. This can be implemented, for example, by a corresponding touch key being available on some or all of the menu views. Thus, a user of a medical device can easily and quickly arrive at certain information and/or input options, largely independently of which menu view is being displayed at the moment.

Figure 1:
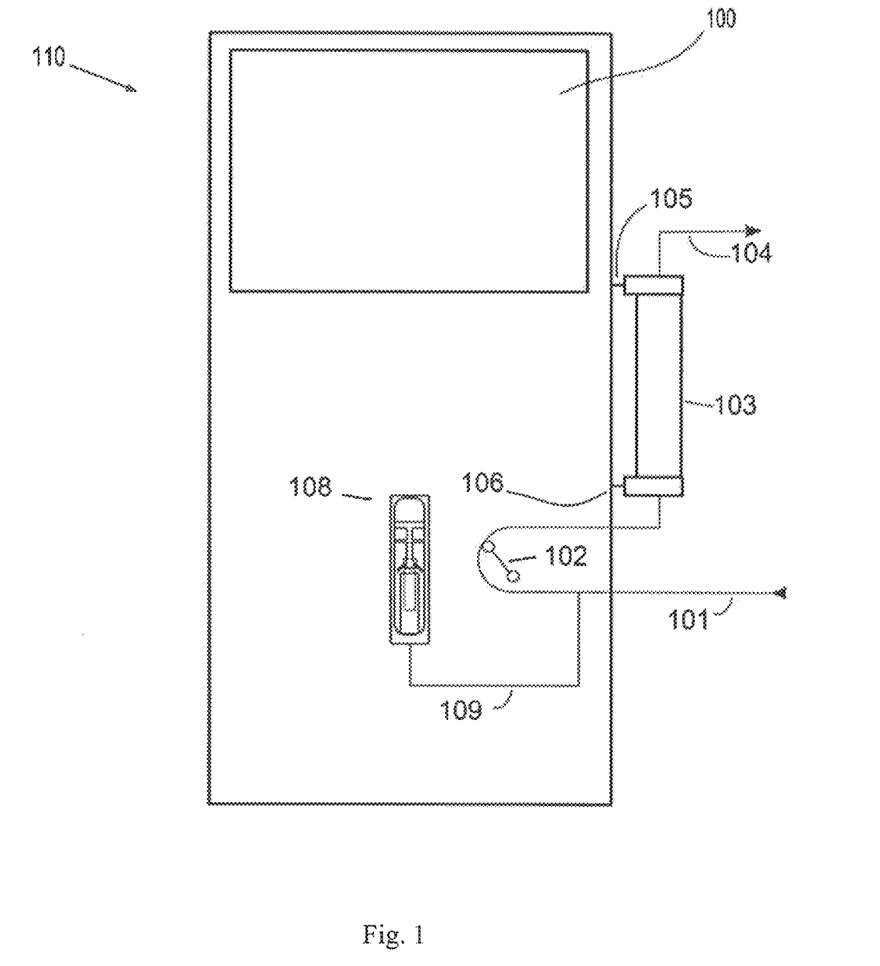
FIG. 1 shows an example of a medical device according to the prior art, which is embodied as a hemodialysis machine.

FIG. 1 shows a hemodialysis machine as an example of a medical device shown schematically. The hemodialysis machine 110 shows indications of parts of an extracorporeal blood circulation with an arterial blood line 101, which drains off the blood of a patient (not shown). The blood pump 102 conveys the blood through a dialysis filter 103, which is equipped with a semipermeable membrane that separates the extracorporeal blood circulation from a dialysis circulation in a semipermeable manner. The treated blood is returned to the patient through the venous line 104. Dialysate is pumped by way of the dialysate 105 and 106 through the dialysis filter 103, where it undergoes diffusive mass exchange with the patient's blood through the semipermeable membrane of the dialysis filter 103. If a pressure gradient is additionally established from the blood side of the dialysis filter to the dialysate side of the patient, plasma water is forced out of the blood and into the dialysate. Water can be withdrawn from the patient in this way. The dialysate is produced in the hemodialysis machine 110 and is discarded after each use. To prevent blood from coagulating in the extracorporeal blood circulation, an anticoagulant agent is added to the blood. This is shown in FIG. 1 with the heparin pump 108, which is embodied as an injection pump that conveys heparin as an anticoagulant into the arterial blood line 101 through the line 109.

The hemodialysis machine 110 is equipped with a touchscreen display 100. The touchscreen display 100 serves as a graphical user interface, which is equipped for input and output of information. A graphical user guide, for example, a graphical user interface (GUI), is embodied on this touchscreen display 100 for operation of the dialysis machine 110.

Figure 2:
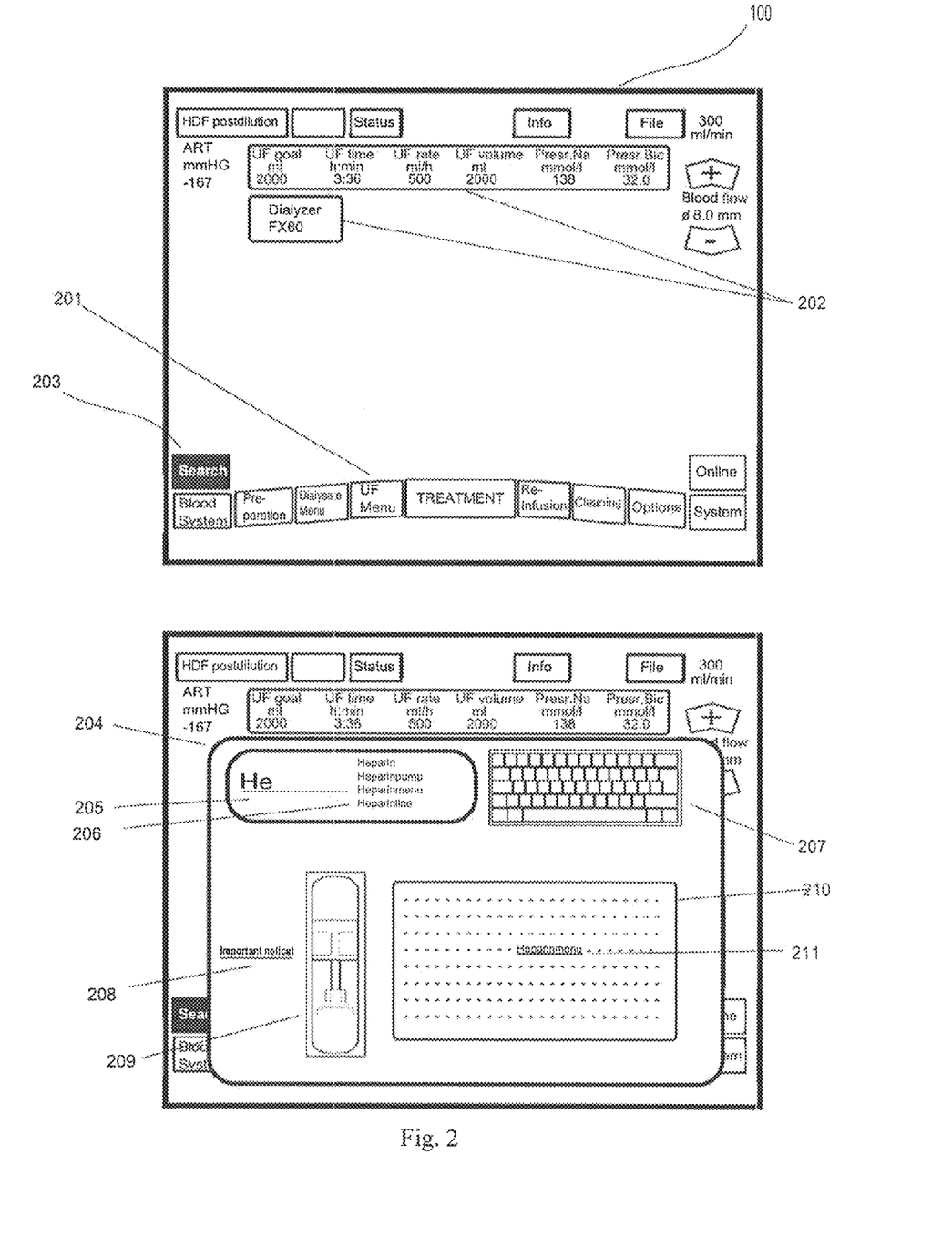
FIG. 2 shows as an example display screen contents of a user interface of a medical device according to the invention.

FIG. 2 shows the display screen contents of the graphical user interface according to the invention as an example. The user interface shown here has the structure a menu, for example, wherein it is possible to switch from a current view of the user interface to additional views, for example, submenus.

A typical user interface of a dialysis machine is shown in the upper screen view of FIG. 2. This shows regions, which display information about the treatment currently underway, such as the regions 202, which show information about the dialysis filter used (FX60) as well as current measured values or parameters, such as the total amount of plasma water to be withdrawn (2000 mL in FIG. 2) or the ultrafiltration rate (500 per hour in FIG. 2).

In addition, entries into the user interface can also be made by way of touch surfaces and/or touch keys, such as those labeled as 201 in FIG. 2, to arrive at other views and/or menus, for example.

In accordance with the present teaching, the user interface has a search function, which can be activated in FIG. 2 by touching the touch key 203.

The lower half of FIG. 2 illustrates the situation after activation of the search function as an example. A window 204 appears, partially covering the view below it. The user can enter text strings into the user interface by means of a virtual keypad 207. The entries are displayed at 205.

A text string that has been input can be searched within files to which the medical device has data access.

It is possible to provide for a selection of text strings that are at least a partial match with the term entered with regard to how they are written or spoken to be displayed already during the input of the text string (FIG. 2, 206). A text string selected from such text strings displayed in this way will then be discussed as the text string entered into the search function.

It is also possible to provide for automatic correction of spelling errors to he carried out during the input. For example, if a user inadvertently inverts the sequence of letters at one location in a text string, it is nevertheless possible to provide that a selection of text strings that at least partially match the term written correctly with regard to how it is written or pronounced. In implementation of such embodiments those skilled in the art will make use of the methods of autocorrection known from word processing programs, for example.

Such text strings discovered in the files being searched are displayed on the user interface.

The user can select a certain text string from the text strings 206 displayed by touching a text string, for example. Then one or more excerpts of the file containing the term selected are displayed. For example, the text string "heparin pump" is selected in FIG. 2, whereupon an excerpt of the file represented by broken horizontal lines, including the term "heparin menu" is displayed in a region 210 (211, FIG. 2 in plain text and underlined).

For example, the text may be taken from operating instructions stored in a file. However, the text may also be taken from any other file, for example, a technical handbook. It is possible to provide that the user can select between a plurality of excerpts of the file and a plurality of files containing the selected term. This may take place, for example, by means of a list of short text passages from various documents from which the user can make a selection. Another embodiment provides that the user can retrieve a plurality of excerpts from the file or a plurality of files containing the selected term, one after the other, by means of a control command, for example, a user input on the user interface.

It is irrelevant for the present teaching where the at least one file pertaining to the medical device is stored. It is important that the control unit has access to it. Thus the at least one file may be stored in an internal memory of the medical device. Another embodiment provides that the at least one file is stored in another device, for example, in a central computer or in a central memory, for example, a so-called cloud storage, and that the medical device can access the at least one file over a network connection.

External storage in external devices enables a plurality of medical devices to have access to the at least one file over network connections. If a file stored in such a way is amended, this automatically has an effect on all the medical devices connected to the external device(s) over a network connection. This permits updating of the file simultaneously for a plurality of medical devices.

In addition, it is possible to provide for the at least one file to also include images or drawings that have a reference to the selected term. For example, the illustration 209 in FIG. 2 shows a heparin pump.

Likewise, messages or references to messages, which themselves refer to the selected text passage or the selected excerpt of the file, can also be displayed (208, FIG. 2). This makes is possible to provide the user with additional information that is not contained in the normal documents such as operating instructions or technical handbooks to make it accessible to the user. For example, the message is displayed by selecting the reference to a message (208) by touch. Such messages may contain, for example, current findings obtained by operation of the medical device and of which the user is to be made aware.

Such messages can also be stored in files to which the medical device has data access in accordance with the present teaching.

In general, in accordance with the present teaching, the display of text, images or drawings can in general also take place via an Internet browser, in particular if a so-called hyperlink to web pages of the Internet is activated by selecting the terms displayed.

The user can select text passages or graphics in the display portion of the file. In FIG. 2, the fact that the term 211 can be selected is characterized by underlining it. Any other characterization, for example, the color of the terms can also be used to display the fact that it can be selected.

Figure 3:
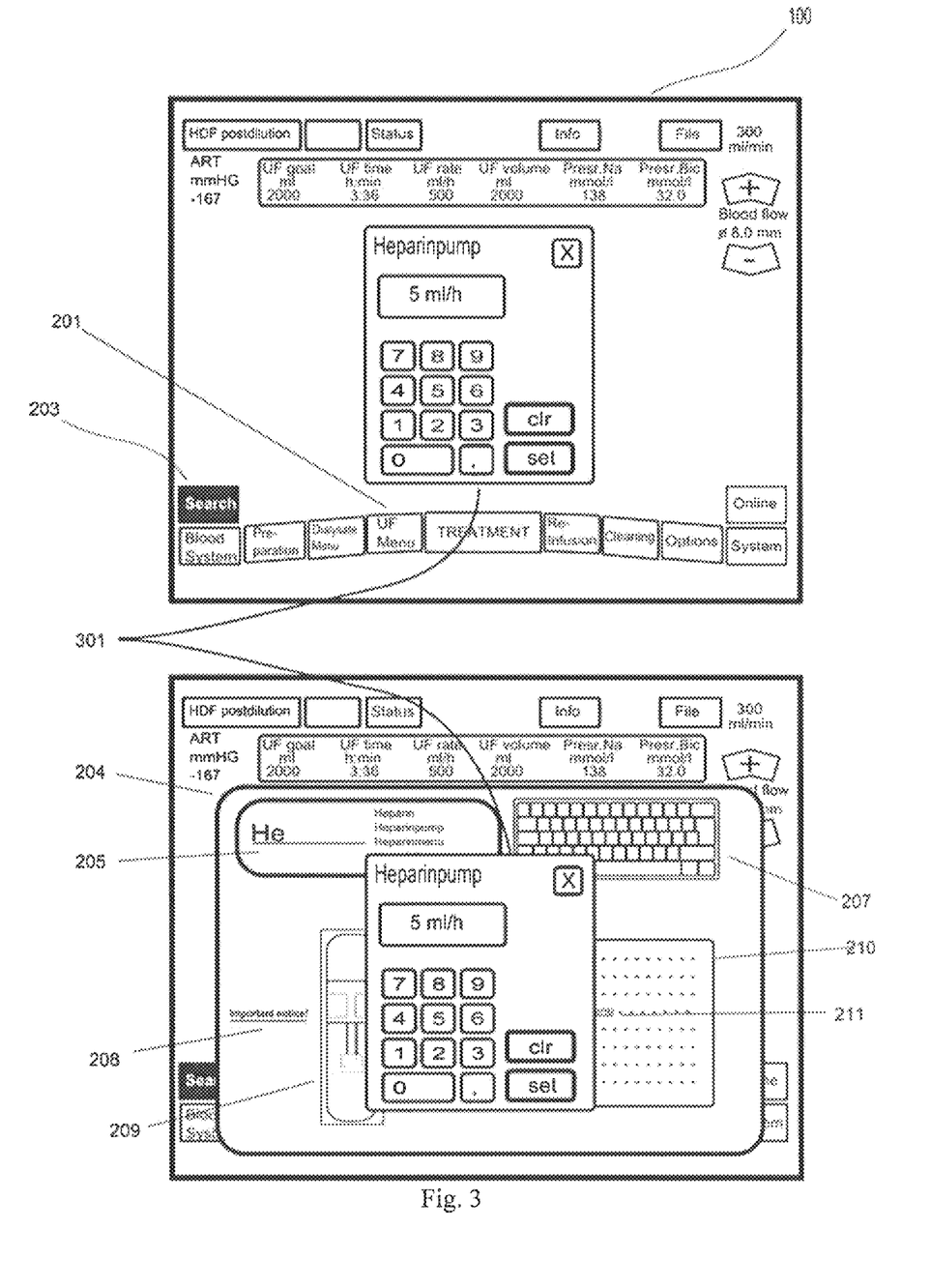
FIG. 3 shows another example of display screen contents of a user interface of a medical device according to the invention.

By selecting a text passage or graphic in the displayed passage, the user is given additional opportunities to retrieve information or to enter information into the user interface as shown in FIG. 3.

The upper portion of the diagram in FIG. 3 shows a first embodiment of how the search function is terminated, after selecting the term 211, and the menu for the display and setting of the heparin pump function is retrieved.

In another embodiment, shown in the lower portion of the diagram in FIG. 3, the search function is not terminated. The menu for the display and setting of the heparin pump function here covers parts of the window 204.

In another embodiment, not shown in FIGS. 2 and 3, after entering a text string into the search function, the menu 301 for display and setting of a parameter of an operating component is retrieved as long as the selected text string relates to this operating component, directly through selection of a text string 206, which is displayed by the search function and can be selected.

The display of an excerpt of the file pertaining to the selected text string (210) and the selection of a text passage 211, which is displayed there and pertains to the operating component, are not absolutely necessary in this embodiment.

In an alternative embodiment, the display of an excerpt of the file pertaining to the selected text string can take place in parallel with the retrieval of the menu 301 for the display and setting of a parameter of an operating component. In contrast with the diagram in FIG. 3 below, this preferably takes place in such a way that the menu 301 for the display and setting of a parameter of an operating component and the display of the excerpt of the file pertaining to the selected text string in window 210 are not positioned to overlap with the graphical user interface. This ensures complete readability of the information in the displayed excerpt of the file pertaining to the selected text string in the window 210 with simultaneous operability of menu 301 for the display and setting of a parameter of an operating component.

In all cases, the user has the option of viewing or setting the operating parameters of the operating component of interest for the user (heparin flow and pump in FIGS. 2 and 3) rapidly and in an uncomplicated manner.

Thus, the user need not know where access to this operating parameter is possible in the menu structure of the user interface. Due to the search function, which can be retrieved from any location within the menu structure of the user interface in one embodiment, it is possible to conduct a search for the operating component and the menu for the display, and setting of the operating parameters of the operating component in the search can be retrieved by selecting the operating component and/or a text passage or a graphic within the excerpt of the file that pertains to the operating component and is displayed.

In addition, it is possible to provide that the display of information or providing input options for parameters depends on authorization of the user that has been previously disclosed to the medical device. It is thus possible to provide that certain people can see information but cannot alter the operating parameters. For example, it is possible to provide that the nursing staff can see the information about the blood pump rate but cannot have the option of readjusting this information, whereas physicians do have this option.

This ensures that only authorized persons can perform certain settings on the medical device. The information display can also be made to depend on the authorization of the user. For example, a more extensive selection of text strings (206) can be made available to physicians than to nursing personnel.

For input of the user's authorization, the medical device may have an authorization device, which can have any desired design. For example, the medical device can be equipped with a card reader. Such a card reader is used for entering the information stored on a so-called electronic SmartCard and may include information about the person, for example, the degree of authorization. The operating person can thus be authorized by entering the SmartCard he or she carries on the medical device.

According to the present invention, the medical device can also be switched to various operating modes through such an authorization. For example, a service technician through his authorization on the medical device can put the medical device in a service mode by allowing access to a variety of setting options and information about the diagnosis, setting and maintenance of the medical device adapted specifically to this operating mode. Other operating modes, which are associated with adapted graphical user interfaces, pertain to the operation by application consultants, trainers or developers of the medical device, for example.

Figure 4:
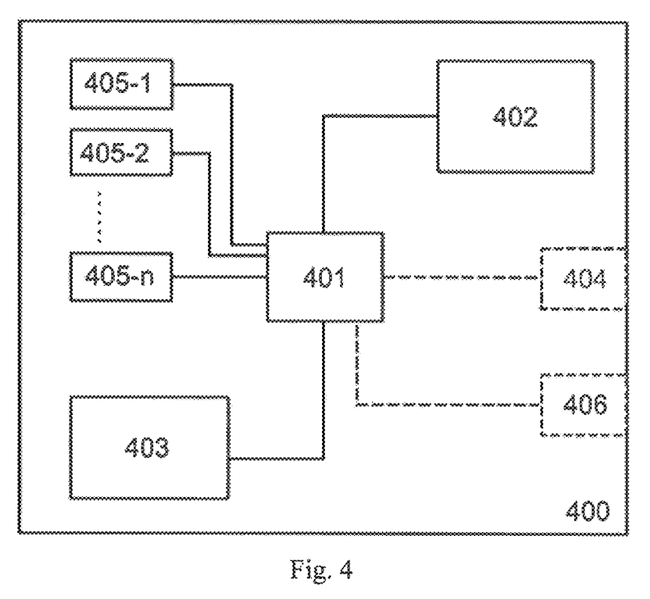
FIG. 4 shows a basic design of a medical device according to the invention.

FIG. 4 shows an example of a schematic design of a medical device 400 according to the present teaching.

The medical device 400 comprises at least one control unit 401. Medical devices often have a plurality of control devices, often embodied as processors or microcontrollers. It is irrelevant for the present teaching whether the methods described here are carried out by a single control unit or a plurality of control units.

The control unit 401 has a data connection to other components. Data, for example, control commands or parameter values, is exchanged over these connections.

In addition, the medical device 400 has a user interface 402 by means of which the information can be input and output. Such a user interface 402 is a touchscreen display in one embodiment.

For the user interface 402, it is does not matter whether the input and output options are combined in single device, as is the case in a touchscreen display, for example, or whether the input and output of information take place by means of separate devices, for example, by a conventional display screen in combination with a separate touch-sensitive surface, a so-called touchpad. In light of the disclosure of the present invention, a user interface may also include separate input and output devices.

In addition, the medical device 400 comprises one or more operating components 405-1, 405-2 through 405-*n*, such as a pump, a valve or a sensor, for example.

An indirect connection of an operating component 405-*x* to the control unit 401 means that a data connection is not directly present but instead, for example, additional devices are connected in between fix processing the data. For example, analog signals from sensors can be converted to digital signals by an intermediate analog/digital converter that is connected in between, and these to digital signals are then sent to the control unit.

The medical device 400 has an internal memory 403, in which software for programming the control unit 401 can be stored. In addition, any data such as documents pertaining to the medical device, for example, can be stored in digital form as files in the memory 403.

In addition, the medical device 400 may comprise a network interface 404. The control unit 401 can access other devices, such as a central computer or a cloud storage, for example, over a network connection in order to gain access to one or more files pertaining to the medical device in the manner already described.

However, access to the internal memory can also be acquired from the outside via the network interface in order to install new software or to save or update one or more files that pertain to the medical device and may optionally be kept there.

The network interface may be embodied as a hardwired interface, for example, according to the RJ45 standard, or as a wireless interface (wireless local area network (WLAN), Bluetooth, infrared, etc.).

In addition, the medical device may also comprise an authorization device 406, over which the user's authorization can be input. Such an authorization device is, for example, a card reader, which can enter memory cards (magnetic memory cards, SmartCards, etc.), wherein the information stored on the memory card is characteristic of the identity of the owner of the memory card. Other authorization devices include, for example, iris scanners, fingerprint scanners, radio-frequency identification (RFID) readers, etc.

Figure 5:
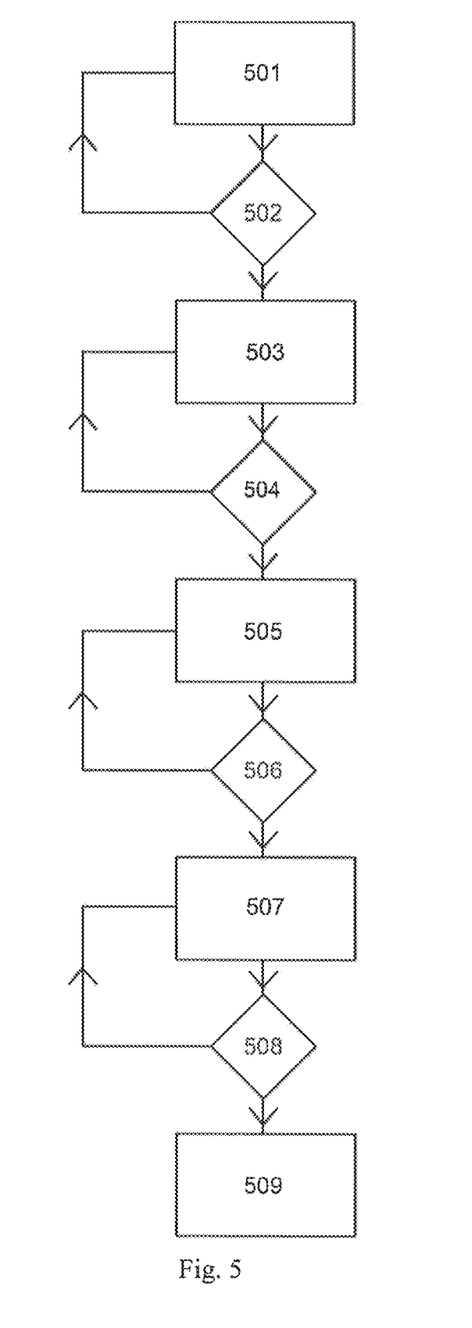
FIG. 5 shows a flow chart of a method according to the invention.

FIG. 5 shows a flow chart of a method in accordance with the present teaching.

In step 501, information pertaining to the medical device and displaying input options for adjustable parameters is output on the graphical user interface. A corresponding screen view is shown at the top of FIG. 2.

As a rule, not all the information that is adjustable and/or can be output can be input and/or output simultaneously on a display screen. A display screen here is understood to refer to the totality of the screen display at any point in time. If the screen display changes subsequently, another screen is displayed. In order to increase comprehensibility, these are not all displayed simultaneously on a display screen since there is often a great deal of information and there are a great many adjustable operating parameters for medical devices. Information and input options for adjustable operating parameters are often summarized thematically here and displayed within a few menus.

In addition, step 501 includes enabling the selection of a search function by means of which text strings can be input. The choice of a search function is enabled, for example, by keeping a corresponding touch key (203) on all menu views or on a plurality of menu views.

In step 502, a check is performed as to whether the search function is selected, for example, by touching the corresponding touch key (203). If that is the case, then step 503 takes place. If no search function is selected, then step 501 is carried out further.

In step 503, the search function is activated. This can take place, for example, by opening the window 204.

In step 504, an entry into the search function is checked. If no entry is detected, then step 503 is carried out further. If an entry is detected, then in step 505, there is a search for the input text string or parts thereof or for text strings that correspond at least in part to the term entered or parts thereof with regard to how it is written or how it is spoken. This search takes place within one or more files that are accessible to the medical device. The memory site of these files does not play a role here but it is important that the medical device has access to these files in the data technology. Likewise, in step 505, the text strings that are selectable are displayed. In the lower view of the screen in FIG. 2, the display of the terms that have been found is characterized by the reference numeral 206.

In step 506, the acknowledgement of a selection of a certain text string from the text strings found by the search operation takes place in step 505. If no selection is detected, then step 505 is carried out further. If a selection is detected, then the display of the selected excerpt of the one or more files containing the selected text string takes place in step 507 (FIG. 2, reference numerals 210 and 211). Parts of the excerpt displayed pertaining to the operating component can be selected. This is characterized, for example, by underlining the corresponding part (for example, "heparin menu," bottom of FIG. 2).

A check is performed in step 508 to ascertain whether a selectable portion within the excerpt displayed of one or more files is selected. If no selection is detected, then step 507 is carried out further. If such a selection is detected, then in step 509 the display of operating parameters of the respective operating component and/or of at least one output variable that is created and read out by the respective operating component is displayed on the graphical user interface. Alternatively, an input option for adjustable operating parameters of the respective operating component can be displayed on the graphical user interface (FIG. 3, reference numeral 301).

Through the present invention, the operation of medical devices is simplified and made safer. This gives the inexperienced user in particular an opportunity to find information rapidly within the structure of a graphical user interface as well as to rapidly see or enter parameters of operating component of the medical device. Operation of the medical device is thus simplified and the operational reliability is increased.

It will be appreciated by those of skill in the art that the execution of the various machine-implemented processes and steps described herein may occur via the computerized execution of processor-executable instructions stored on a non-transitory computer-readable medium, e.g., random access memory (RAM), read-only memory (ROM), programmable read-only memory (PROM), volatile, nonvolatile, or other electronic memory mechanism. Thus, for example, the operations described herein performed by computing devices and components thereof may be carried out according to stored instructions and/or installed applications.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

The invention claimed is:

1. A medical device, comprising:
    a display configured to provide a user interface;
    an actuator or sensor; and
    a control unit, connected to the actuator or sensor and to the display;
    wherein the control unit is configured to:
        control the user interface to display a touch key corresponding to a search function;
        receive, via the user interface, user input corresponding to selection of the touch key corresponding to the search function;
        control the user interface to display a search window in response to receiving the user input corresponding to selection of the touch key corresponding to the search function, wherein the search window comprises a search field;
        receive, via the user interface, user input corresponding to entry of a partial text string into the search field;
        control the user interface to display one or more full text strings corresponding to the partial text string in response to receiving the user input corresponding to entry of the partial text string, wherein the one or more full text strings include a full text string corresponding to the actuator or sensor;
        receive, via the user interface, user input corresponding to selection of the full text string corresponding to the actuator or sensor;
        control the user interface to display text passages and/or graphics relating to the actuator or sensor in response to receiving the user input corresponding to selection of the full text string corresponding to the actuator or sensor;
        receive, via the user interface, user input corresponding to selection of a displayed text passage or graphic relating to the actuator or sensor;
        control the user interface to display an actuator or sensor interface corresponding to the actuator or sensor in response to receiving the user input corresponding to selection of the displayed text passage or graphic relating to the actuator or sensor;
        receive, via the user interface, user input on the actuator or sensor interface for adjustment of an operating parameter relating to the actuator or sensor; and
        adjust the operating parameter relating to the actuator or sensor based on the received user input for adjustment of the operating parameter relating to the actuator or sensor.

2. The medical device according to claim 1, further comprising:
    a memory, wherein at least one file comprising the text passages and/or graphics is stored in the memory.

3. The medical device according to claim 2, further comprising:
    a network interface, wherein the memory is configured to be written based on data received via the network interface.

4. The medical device according to claim 1, further comprising:
    a network interface;
    wherein the control unit is configured to access at least one file comprising the text passages and/or graphics via the network interface.

5. The medical device according to claim 1, further comprising an acoustic input device configured to receive acoustic information and/or an acoustic output device configured to output acoustic information.

6. The medical device according to claim 1, wherein the medical device is a blood treatment machine.

7. The medical device according to claim 1, wherein the control unit is further configured to terminate the search function such that the search window is no longer displayed prior to controlling the user interface to display an actuator or sensor interface corresponding to the actuator or sensor.

8. The medical device according to claim 1, wherein controlling the user interface to display the actuator or sensor interface corresponding to the actuator or sensor comprises overlaying the actuator or sensor interface over the search window.

9. The medical device according to claim 1, wherein the actuator or sensor comprises a heparin pump;
    wherein the actuator or sensor interface corresponding to the actuator or sensor comprises a user interface window for receiving a pump rate; and
    wherein adjusting the operating parameter relating to the actuator or sensor comprises adjusting the pump rate of the heparin pump.

10. The medical device according to claim 1, wherein the control unit is further configured to control the user interface to display the touch key corresponding to the search function in a plurality of menu views provided via the user interface.

11. The medical device according to claim 1, wherein the control unit is further configured to control the user interface to display the touch key corresponding to the search function together with information about a treatment being provided by the medical device that is currently underway.

12. A method for outputting information pertaining to a medical device, the method comprising:
  displaying, by the medical device, a touch key corresponding to a search function;
  receiving, by the medical device, user input corresponding to selection of the touch key corresponding to the search function;
  displaying, by the medical device, a search window in response to receiving the user input corresponding to selection of the touch key corresponding to the search function, wherein the search window comprises a search field;
  receiving, by the medical device, user input corresponding to entry of a partial text string into the search field;
  displaying, by the medical device, one or more full text strings corresponding to the partial text string in response to receiving the user input corresponding to entry of the partial text string, wherein the one or more full text strings include a full text string corresponding to the actuator or sensor;
  receiving, by the medical device, user input corresponding to selection of the full text string corresponding to the actuator or sensor;
  displaying, by the medical device, text passages and/or graphics relating to the actuator or sensor in response to receiving the user input corresponding to selection of the full text string corresponding to the actuator or sensor;
  receiving, by the medical device, user input corresponding to selection of a displayed text passage or graphic relating to the actuator or sensor;
  displaying, by the medical device, an actuator or sensor interface corresponding to the actuator or sensor in response to receiving the user input corresponding to selection of the displayed text passage or graphic relating to the actuator or sensor;
  receiving, by the medical device, user input on the actuator or sensor interface for adjustment of an operating parameter relating to the actuator or sensor; and
  adjusting, by the medical device, the operating parameter relating to the actuator or sensor based on the received user input for adjustment of the operating parameter relating to the actuator or sensor.

13. The method according to claim 12, wherein one or more of the user inputs are received via an acoustic input device.

14. The method according to claim 12, wherein the medical device is a blood treatment machine.

15. The method according to claim 12, further comprising:
  outputting acoustic information via an acoustic output device.

16. The method according to claim 12, further comprising:
  prior to controlling the user interface to display an actuator or sensor interface corresponding to the actuator or sensor, terminating the search function such that the search window is no longer displayed.

17. The method according to claim 12, wherein displaying the actuator or sensor interface corresponding to the actuator or sensor comprises overlaying the actuator or sensor interface over the search window.

18. The method according to claim 12, wherein the actuator or sensor comprises a heparin pump;
  wherein the actuator or sensor interface corresponding to the actuator or sensor comprises a user interface window for receiving a pump rate; and
  wherein adjusting the operating parameter relating to the actuator or sensor comprises adjusting the pump rate of the heparin pump.

19. The method according to claim 12, further comprising:
  displaying the touch key corresponding to the search function in a plurality of menu views provided via the user interface.

20. The method according to claim 12, wherein the touch key corresponding to the search function is displayed together with information about a treatment being provided by the medical device that is currently underway.

21. A non-transitory computer-readable medium having processor-executable instructions stored thereon for outputting information pertaining to a medical device, wherein the processor-executable instructions, when executed, facilitate:
  displaying, by the medical device, a touch key corresponding to a search function;
  receiving, by the medical device, user input corresponding to selection of the touch key corresponding to the search function;
  displaying, by the medical device, a search window in response to receiving the user input corresponding to selection of the touch key corresponding to the search function, wherein the search window comprises a search field;
  receiving, by the medical device, user input corresponding to entry of a partial text string into the search field;
  displaying, by the medical device, one or more full text strings corresponding to the partial text string in response to receiving the user input corresponding to entry of the partial text string, wherein the one or more full text strings include a full text string corresponding to the actuator or sensor;
  receiving, by the medical device, user input corresponding to selection of the full text string corresponding to the actuator or sensor;
  displaying, by the medical device, text passages and/or graphics relating to the actuator or sensor in response to receiving the user input corresponding to selection of the full text string corresponding to the actuator or sensor;
  receiving, by the medical device, user input corresponding to selection of a displayed text passage or graphic relating to the actuator or sensor;
  displaying, by the medical device, an actuator or sensor interface corresponding to the actuator or sensor in response to receiving the user input corresponding to selection of the displayed text passage or graphic relating to the actuator or sensor;
  receiving, by the medical device, user input on the actuator or sensor interface for adjustment of an operating parameter relating to the actuator or sensor; and
  adjusting, by the medical device, the operating parameter relating to the actuator or sensor based on the received user input for adjustment of the operating parameter relating to the actuator or sensor.

* * * * *